United States Patent [19]

Tsujitani et al.

[11] Patent Number: 4,992,442
[45] Date of Patent: Feb. 12, 1991

[54] PYRROLO(3,2-E)PYRAZOLO(1,5-A)PYRIMI-DINE DERIVATIVE AND MEDICINE COMPRISING THE SAME

[75] Inventors: Michihiko Tsujitani; Kenichi Kishii; Masato Inazu; Toshihiro Morimoto; Yoshiaki Motoki, all of Yokohama; Ichiro Matsuo, Machida, all of Japan

[73] Assignee: Pola Chemical Industries Inc., Japan, Shizuoka, Japan

[21] Appl. No.: 416,524

[22] Filed: Oct. 3, 1989

[30] Foreign Application Priority Data

Oct. 13, 1988 [JP] Japan .................................. 63-258084
Jan. 20, 1989 [JP] Japan ..................................... 1-11555
Jan. 20, 1989 [JP] Japan ..................................... 1-11556

[51] Int. Cl.$^5$ ................... A61K 31/505; C07D 401/14
[52] U.S. Cl. ................................. 514/267; 514/233.2; 544/115; 544/251
[58] Field of Search ................. 544/251, 115; 514/267, 514/233.2

[56] References Cited

PUBLICATIONS

Ernst Tenor et al, Chem. Abst. 67-90830f (1967).

Primary Examiner—Cecilia Shen
Attorney, Agent, or Firm—Oblon, Spivak, McClelland, Maier & Neustadt

[57] ABSTRACT

Pyrrolo[3,2-e]pyrazolo[1,5-a]pyrimidine derivatives are disclosed. The compounds are represented by the formula (I),

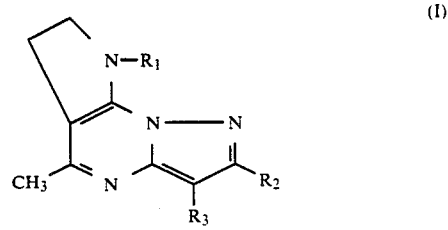

wherein $R_1$ and $R_2$ individually represent a hydrogen atom, a linear or branched alkyl group which may have a substituent, a cycloalkyl or phenyl group which may have a substituent, or a heterocyclic group which may have a substituent, and $R_3$ is a hydrogen atom or a cyano group. The compounds have excellent circulatory disease curing activities as well as bronchodilation activities.

14 Claims, No Drawings

PYRROLO(3,2-E)PYRAZOLO(1,5-A)PYRIMIDINE DERIVATIVE AND MEDICINE COMPRISING THE SAME

BACKGROUND OF THE INVENTION

1. Field of the Invention

This invention relates to pyrrolo[3,2-e]pyrazolo[1,5-a]pyrimidine derivatives and their salts possessing excellent vasodilative, antihypertensive, antihyperlipemia, platelet aggregation suppressing, $Ca^{++}$ blocking, and bronchodilative activities, and to a medicine comprising a pyrrolo[3,2-e]pyrazolo[1,5-a]pyrimidine derivative or its salt as an effective component.

2. Description of the Background Art

In today's society in which life-spans are prolonged circulatory diseases have become a major cause of death along with malignant tumors.

One effective way of treating circulatory diseases is to lower the blood pressure by a vasodilator and to promote the blood circulation. Suppressing platelet aggregation is a useful way of inhibiting the formation of arterial thrombosis. Many compounds possessing $Ca^{++}$ blocking activity also have an antiarrhythmic activity. Moreover, many of the diseases relating to circulation are closely associated with each other.

Accordingly, development of a medicine which is effective for all of these circulatory diseases has been desired.

On the other hand, bronchial asthma is a disease involving abnormal contraction of bronchial smooth muscle, swelling of bronchial mucosa, secretion of mucus, and the like, all of which are considered to be caused by various exogenous and endogenous factors, even though the mechanisms involved remain to be elucidated. For this reason, a symptomatic therapy using medicines rather than a therapy eliminating the cause of the disease are mostly used.

Major medicines currently used for curing bronchial asthma are β-receptor stimulants. The only other medicine used for this purpose is theophylline. These medicines, however, have many side effects, and, because of this, their doses and the period of administration have to be limited.

Development of medicines for curing bronchial asthma, e.g. a bronchodilator, with minimal side effect has therefore been sought.

In view of this situation, the present inventors have undertaken extensive studies and found that compounds represented by the following formula (I) had excellent circulatory disease curing activities as well as bronchodilation activities. This finding has led to the completion of the present invention.

SUMMARY OF THE INVENTION

Accordingly, an object of the present invention is to provide a pyrrolo[3,2-e]pyrazolo[1,5-a]pyrimidine derivative represented by the formula (I),

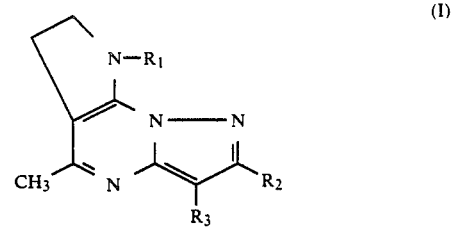

wherein $R_1$ and $R_2$ individually represent a hydrogen atom, a linear or branched alkyl group which may have a substituent, a cycloalkyl or phenyl group which may have a substituent, or a heterocyclic group which may have a substituent, and $R_3$ is a hydrogen atom or a cyano group.

Another object of the present invention is to provide a medicine for curing circulatory diseases and for curing bronchiectasis comprising a pyrrolo[3,2-e]pyrazolo[1,5-a]pyrimidine derivative as an effective component.

Other objects, features and advantages of the invention will hereinafter become more readily apparent from the following description.

DETAILED DESCRIPTION OF THE INVENTION AND PREFERRED EMBODIMENTS

Given as examples of a heterocyclic group for $R_1$ and $R_2$ in formula (I) of this invention, are piperidyl group, piperazinyl group, morpholinyl group, thienyl group, and the like. Given as examples of a linear or a branched alkyl group for $R_1$ and $R_2$ in formula (I), are alkyl groups having from 1 to 14 carbon atoms such as methyl group, ethyl group, n-propyl group, n-butyl group, iso-butyl group, sec-butyl group, n-hexyl group, octyl group, decanyl group, and the like. Given as examples of a cycloalkyl group are, groups having from 4 to 8 carbon atoms such as cyclopentyl group, cyclohexyl group, and the like. Given as examples of substituents for these groups are hydroxyl group, alkoxy group, nitro group, primary-, secondary-, or tertiary-amino group, carboxyl group, cycloalkyl group, phenyl group, substituted phenyl group, halogen atom, heterocyclic group, e.g. pyrrol, pyrrolidine, pyridine, piperidine, imidazole, imidazoline, morpholine, pyrrolidone, etc., and the like.

The compound of formula (I) of this invention can be produced according to the process shown by the following reaction scheme:

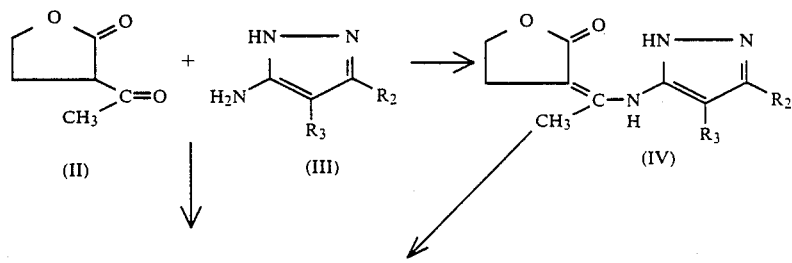

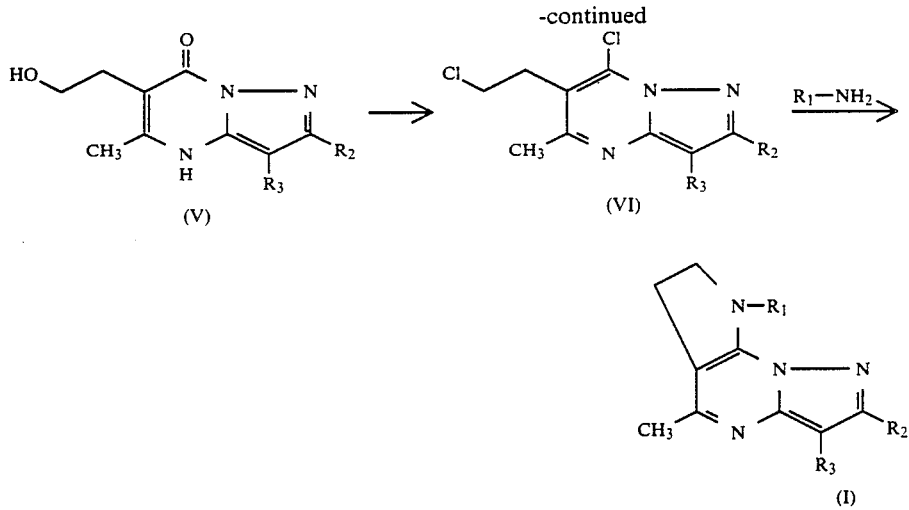

wherein $R_1$, $R_2$, and $R_3$ have the same meanings as defined above.

Specifically, a dehydration and condensation reaction is carried out using an α-acethyl-T-butyrolactone (A.B.L) [Compound (II)] and a 5-aminopyrazole [Compound (III)] to produce Compound (IV). Then, a lactone ring opening/closing reaction is effected on Compound (IV) to obtain 6-(2-hydroxyethyl)-5-methyl-pyrazolo[1,5-a]pyrimidine-7(4H)-one [Compound (V)]. The compound obtained is halogenated to produce 7-halo-6-(2-haloethyl)-5-methylpyrazolo[1,5-a]pyrimidine [Compound (VI)], which is reacted with an amine to produce Compound (I) of this invention.

Alternatively, Compound (V) can be directly produced by reacting A.B.L [Compound (II)] with 5-aminopyrazol [Compound (III)] while refluxing under heating in the presence of an appropriate solvent, e.g. dimethylformamide, xylene, or acetic acid.

The production of Compound (IV) from Compound (II) and Compound (III) can be performed, for example, by the reaction of Compound (II) and Compound (III) in the presence of a catalyst such as Lewis acid, e.g. trifluoroborane, in a suitable solvent, e.g. an alcohol.

The reaction for producing Compound (V) from Compound (IV) is carried out in a mixed solution of water and a tertiary amine, e.g. triethylamine, N-methylmorpholine, or pyridine, in a caustic alkaline solution or in an aqueous alcohol.

Compound (VI) can be produced from Compound (V) by reacting Compound (V) with a halogenating agent, e.g. phosphorus oxychloride or phosphoric pentachloride, under heating, in the absence or in the presence of a solvent such as tetrachloroethane, ethylene dichloride, chloroform, trichloroethylene, benzene, chlorobenzene, or the like. A catalyst such as N-methylmorpholine, triethylamine, pyridine, dimethylaniline, dimethylformamide, or the like can be used in this reaction.

Compound (I) is produced from Compound (VI) by reacting Compound (VI) with an amine in a solvent, e.g. an alcohol, dimethylformamide, dimethylsulfoxide, or methyl ethyl ketone, in the presence of a deoxidizing agent such as sodium carbonate, potassium carbonate, triethylamine, pyridine, or the like.

Compound (I) of this invention thus obtained can be changed to a pharmaceutically acceptable organic or inorganic salt. It can also be made into a quaternary salt by the reaction with alkyliodide or the like.

As shown by experimental examples hereinafter, Compound (I) of the present invention has excellent vasodilative activity, coronary blood flow increasing activity, bronchodilator activity, antihyperlipidemia activity, platelet aggregating activity, antihypertensive activity, $Ca^{++}$ antagonistic activity, and the like, and is highly safe. It is thus useful as a medicine for circulatory diseases and also as a bronchodilator.

When Compound (I) of this invention is administered to humans, it is preferable that the compound be orally administered two or three times in a day at a dose, for example, 10 to 100 mg per day, depending on the age or the symptom of the patient.

A medicine for circulatory diseases or a bronchodilator of the present invention can be formed into various preparations, for example, preparations for oral administration such as tablets, capsules, abstracts, troches, liquids, and the like. These preparations can be prepared according to known methods. Specifically, Compound (I) of the present invention is formed into preparations including tablets, capsules, abstracts, or troches, as required, by appropriately formulating excipients such as starch, mannitol, lactose, and the like; binders such as sodium carboxymethylcellulose, hydroxypropylcellulose, and the like; disintegrators such as crystalline cellulose, calcium carboxymethylcellulose, and the like; lubricants such as talc, magnesium stearate, and the like; fluidity improvers such as light anhydrous silicic acid and the like.

Other features of the invention will become apparent in the course of the following description of the exemplary embodiments which are given for illustration of the invention and are not intended to be limiting thereof.

EXAMPLES

EXAMPLE 1

(i) 19.5 g of A.B.L, 60 g of 3-amino-4-cyanopyrazole [synthesized according to *J. Amer. Chem. Soc.* 78, 784 (1956)], 200 ml of anhydrous ethanol, and 5 ml of a $BF_3$-methanol reagent were mixed and stirred at room temperature for one day. Light brown crystals thus produced were collected by filtration, washed with isopropanol, and recrystallized in dimethylformamide-isopropanol to obtain 105 g of 3-{[1-(tetrahydro-2-oxo- 3-furyl)ethylidene]amino}-4-cyanopyrazole [$R_2$=H, $R_3$=CN in formula (IV)] as light brown crystals at a yield of 86.4%.

MS: m/e M+ 218

The following compounds (ii), (iii), (iv), (v), and (vi) were produced according to the same procedures as above.

(ii) 3-{[1-(tetrahydro-2-oxo-3-furyl)ethylidene]amino}-4-cyano-5-methylpyrazole [$R_2$=CH$_3$, $R_3$=CN in formula (IV)]
Yield: 97.7%
Melting Point: 222°–224° C
White crystals
MS: m/e M+ 232

(iii) 3-{[1-(tetrahydro-2-oxo-3-furyl)ethylidene]amino}-5-methylpyrazole [$R_2$=CH$_3$, $R_3$=H in formula (IV)]
Yield: 66.94%
Melting Point: 157°–158° C
White crystals
MS: m/e M+ 207

(iv) 3-{[1-(tetrahydro-2-oxo-3-furyl)ethylidene]amino}-5-phenylpyrazole [$R_2$=C$_6$H$_5$, $R_3$=H in formula (IV)]
Yield: 76.9%
Melting Point: 298°–299° C
Light brown crystals
MS: m/e M+ 269

(v) 3-{[1-(tetrahydro-2-oxo-3-furyl)ethylidene]amino}-5-(3-thienyl)pyrazole [$R_2$=

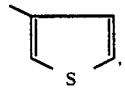

$R_3$=H in formula (IV)]
Yield: 82.0%
Melting Point: 193°–194° C
Light brown crystals
MS: m/e M+ 275

(vi) 3-{[1-(tetrahydro-2-oxo-3-furyl)ethylidene]amino}-5-methylpyrazole [$R_2$=H, $R_3$=H in formula (IV)]
Yield: 99.1%
Melting Point: 132°–137° C
White crystals

EXAMPLE 2

(i-1) 15 g of Compound (IV) [$R_2$=H, $R_3$=CN], 35 ml of water, and 9.7 ml of triethylamine were mixed and stirred at 50° C in a warm bath to obtain a brown solution. After heating for about 5 hours, the reacted solution was allowed to stand at room temperature over night. Precipitations of brown crystals was confirmed. The solution was acidified by adding acetic acid. Deposited crystals were collected and recrystallized in dimethylformamide to obtain 13.5 g of 3-cyano-6-(2-hydroxyethyl)-5-methylpyrazolo[1,5-a]pyrimidine-7(4H)-one [$R_2$=H, $R_3$=CN in formula (V)] as slight brown crystals having a decomposition temperature of 283° C at a yield of 90.0%.

MS: m/e M+ 218

(i-2) An equivalent mol of A.B.L and 3-amino-4-cyanopyrazole in xylene were refluxed under heating at 170° C in an oil bath for 5 hours. The solvent was evaporated until crystals began to deposit. The mixture was cooled and the crystals deposited were collected by filtration to produce Compound (V) [$R_2$=H, $R_3$=CN] at a yield of 52%.

The following compounds (ii), (iii), (iv), (v), and (vi) were produced according to the same procedures as (i-1).

(ii) 3-cyano-2,5-dimethyl-6-(2-hydroxyethyl)pyrazolo[1,5-a]pyrimidine-7(4H)-one [$R_2$=CH$_3$, $R_3$=CN in formula (V)]
Yield: 77.5%
Melting Point: 277°–278° C
White crystals (iii) 2,5-dimethyl-6-(2-hydroxyethyl)pyrazolo[1,5-a]pyrimidine-7(4H)-one [$R_2$=CH$_3$, $R_3$=H in formula (V)]
Yield: 56.8%
Melting Point: 216° C
White needle-like crystals
MS: m/e M+ 207

(iv) 6-(2-hydroxyethyl)-5-methyl-2-phenyl-pyrazolo[1,5-a]-phenylpyrazolo[1,5-a]pyrimidine-7(4H)-one [$R_2$=C$_6$H$_5$, $R_3$=H in formula (V)]
Yield: 88.3%
Melting Point: 307° C (decomposed)
Colorless crystals
MS: m/e M+ 269.1 sl (v) 6-(2-hydroxyethyl)-5-methyl-2-(3-thienyl)-pyrazolo[1,5-a]pyrimidine-7(4H)-one [$R_2$=

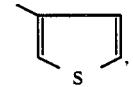

$R_3$=H in formula (V)]
Yield: 79.0%
Melting Point: 310° C (decomposed)
MS: m/e M+ 275

(vi) 2-(2-hydroxyethyl)-5-methylpyrazolo[1,5-a]pyrimidine-7(4H)-one [$R_2$=H, $R_3$=H in formula (V)]
Yield: 85.0%
Melting Point: 234°–238° C
White crystals

EXAMPLE 3

(i) 30 g of Compound (V) [$R_2$=H, $R_3$=CN] and POCl$_3$ were refluxed under heating at 130°–135° C in an oil bath for 4 hours while stirring. Almost all of surplus POCl$_3$ was evaporated under reduced pressure. A red honeylike substance remained was charged into 500 ml of water in which ice flakes were floated. To the cooled solution was added a small amount of saturated sodium carbonate solution to alkalinize the solution. Reddish orange crystals deposited were collected by filtration and washed with water. After the crystals thus obtained were dried with air, they were dissolved in 150 ml of methyl ethyl ketone and 2 g of decolored carbon was added to the solution. The mixture was stirred in a water bath for 30 minutes and filtered. The filtrate was introduced into a chromatographic column packed with alumina (pH=7) which had been activated by methyl ethyl ketone in advance. Finally, 50 ml of methyl ethyl ketone was charged into the column to flow all the developed substances out of the column, and the eluate was concentrated. When crystals just started to deposit, isopropyl ether was added to the concentrate followed by ice-cooling. Yellowish orange crystals thus produced were collected by filtration. The crystals were dissolved in methyl ethyl ketone under heating. To this was again added isopropylether followed by ice-cooling to produce 22.0 g of 7-chloro-6-(2-chloroethyl)-3-cyano-5-methylpyrazolo[1,5-a]pyrimidine [$R_2$=H, $R_3$=CN in formula (VI)] as orange crystals having a melting point of 143°–145° C at a yield of 62.6%.

MS: m/e M+ 254

(ii) To 11.6 g (0.05 mol) of Compound (V) [$R_2$=CH$_3$, $R_3$=CN] were added 23 ml (0.25 mol) of POCl$_3$ and 3 drops of dimethylaniline as a catalyst and the mixture was heated in an oil bath. The mixture once solidified at about 90° C, it was again liquidized with a crimson color at 130° C when heating was continued. The solution were refluxed under heating for 4 hours, followed by evaporating surplus POCl$_3$ under reduced pressure. Red-honeylike substance obtained were extracted with 150 ml of dried chloroform. The extract was poured into 300 ml of ice water. To the cooled solution was added dropwise saturated sodium carbonate solution to alkalinize. The chloroform layer was separated, washed with water, dried over sodium sulfate and filtered. The filtrate was condensed to obtain yellowish orange crystals. The crystals were recrystallized in a mixed solution of methyl ethyl ketone and isopropylether to produce 9.5 g of 7-chloro-6-(2-chloroethyl)-3-cyano-2,5-dimethylpyrazolo[1,5-a]pyrimidine [$R_2$=CH$_3$, $R_3$=CN in formula (VI)] as yellowish orange crystals having a melting point of 113°–115° C at a yield of 70.6%.

MS: m/e M+ 268

The following compounds (iii), (iv), (v), and (vi) were produced according to the same procedures as above.

(iii) 7-chloro-6-(2-chloroethyl)-2,5-dimethylpyrazolo[1,5-a]pyrimidine [$R_2$=CH$_3$, $R_3$=H in formula (VI)]
Yield: 56.1%
Melting Point: 111° C
Yellowish orange crystals
MS: m/e M+ 243

(iv) 7-chloro-6-(2-chloroethyl)-5-methyl-2-phenylpyrazolo[1,5-a]pyrimidine [$R_2$=C$_6$H$_5$, $R_3$=H in formula (VI)]
Yield: 55.6%
Melting Point: 139°–140° C
Yellowish green crystals
MS: m/e M+ 306

(v) 7-chloro-6-(2-chloroethyl)-5-methyl-2-(3-thienyl)-pyrazolo[1,5-a]pyrimidine [$R_2$=

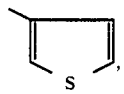

$R_3$=H in formula (VI)]
Yield: 75.3%
Melting Point: 156° C
Yellow crystals
MS: m/e M+ 311

(vi) 7-chloro-6-(2-chloroethyl)-5-methyl-pyrazolo[1,5-a]pyrimidine [$R_2$=H, $R_3$=H in formula (VI)]
Yield: 70.1%
Melting Point: 91°–92° C
Light yellow crystals

EXAMPLE 4

(i) A mixture of 7.0 g (0.0275 mol) of Compound (VI) [$R_2$=H, $R_3$=CN], 5.0 g of anhydrous sodium carbonate, 80 ml of methyl ethyl ketone, and 7 ml of tert-butylamine was refluxed under heating at 85°–90° C in a water bath for 4 hours while stirring. After cooling, the reaction mixture was filtered. A red residue remained was extracted with 100 ml of methyl ethyl ketone. The filtrate together with the extract obtained above was introduced into a chromatographic column packed with 20 g of silica gel (pH 7, 200 mesh) using methyl ethyl ketone and developed. All eluate was concentrated at 60° C under reduced pressure in a water bath. When crystals just started to deposit, isopropyl ether was added in an amount necessary to make the mixture turbid. After cooling the mixture overnight, 4.8 g of 8-tert-butyl-3-cyano-6,7-dihydro-5-methyl-8H-pyrrolo[3,2-e]pyrazolo[1,5-a]pyrimidine [$R_1$=C(CH$_3$)$_3$, $R_2$=H, $R_3$=CN in formula (I)] (Compound 1 of this invention) was obtained as yellowish orange crystals having a melting point of 217°–220° C at a yield of 68.57%.

MS: m/e M+255

(ii-1) 2.7 g (0.01 mol) of Compound (VI) [$R_2$=CH$_3$, $R_3$=CN], 2 ml of triethylamine, 3.2 ml of tert-butylamine, and 15 ml of anhydrous ethanol were placed in a closed tube and heated at 85° C in a water bath for 8 hours. Then the tube was opened, and 100 ml of methyl ethyl ketone was added to the reaction solution. The mixed solution was warmed and subjected to filtration. The filtrate was purified over a chromatographic column packed with 10 g of silica gel (pH=7, 200 mesh) using methyl ethyl ketone in advance. The eluant was then evaporated to obtain 2.4 g of 8-tert-butyl-3-cyano-6,7-dihydro-2,5-dimethyl-8H-pyrrolo[3,2-e]pyrazolo[1,5-a]pyrimidine [$R_1$=C(CH$_3$)$_3$, $R_2$=CH$_3$, $R_3$=CN in formula (I)] (Compound 2 of this invention) as yellowish orange plate crystals having a melting point of 229°–230° C at a yield of 80.0%.

MS: m/e M+269

(ii-2) A mixture of 7.0 g (0.026 mol) of Compound (VI) [$R_2$=CH$_3$, $R_3$=CN], 6 ml of triethylamine, 15 ml of tert-butylamine, 0.1 g of sodium bromide micro-powder, 2.8 g of anhydrous sodium carbonate or potassium carbonate, 30 ml of anhydrous ethanol, and 100 ml of methyl ethyl ketone was reacted at 95° C in an oil bath for 8 hours while stirring. The reaction solution was filtered while it was warm. The filtrate was purified using chromatography according to the same method as above to obtain Compound (I) [$R_1$=C(CH$_3$)$_3$, $R_2$=CH$_3$, $R_3$=CN] at a yield of 78.5%.

(iii) To 4.0 g (0.015 mol) of Compound (VI) [$R_2$=CH$_3$, $R_3$=CN] were added 20 ml of 99.5% ethanol and 20 ml of 28% aqueous ammonia. The mixture which was placed in a closed tube was heated first at 50° C. for 2 hours, then at 70° C for 2 hours, and finally at 95° C for 6 hours. After cooling, the tube was opened and the reaction solution was filtered. Reddish brown crystals thus obtained were washed with ice water, dissolved in dimethylformamide under heating, and cooled with ice water. A small amount of isopropyl alcohol was added for promoting crystal deposition. thus producing 3-cyano-6,7-dihydro-2,5-dimethyl-8H-pyrrolo[3,2-e]pyrazolo [1,5-a]pyrimidine [$R_1$=H, $R_2$=CH$_3$, $R_3$=CN in formula (I)] as reddish brown crystals having a decomposition temperature of 275°–280° C at a yield of 72.0%.

MS: m/e M+213

EXAMPLE 5

(i) A mixture of 88.9 g of Compound (VI) [$R_2$=H, $R_3$=CN], 33.0 g of tert-butylamine, 89 g of anhydrous potassium carbonate, and 700 ml of anhydrous dimethylformamide were stirred at room temperature overnight. To the reaction solution was added 500 ml of chloroform to remove insoluble substances by filtration. The filtrate was condensed under reduced pressure to dryness. The residue was dissolved in chloroform, washed with water, and dried over anhydrous sodium sulfate. The residue from which the solvent was evaporated was recrystallized in benzene to produce 73.6 g of 8-tert-butyl-3-cyano-6,7-dihydro-5-methyl-8H-pyrrolo [3,2-e]pyrazolo[1,5-a]pyrimidine [$R_1$=C(CH$_3$)$_3$, $R_2$=H, $R_3$=CN in formula (I)] having a melting point of 220°–224° C. at a yield of 82.8%.

The following Compounds 3–9 were produced according to the same procedures as above.

(ii) 8-butyl-3-cyano-6,7-dihydro-5-methyl-8H-pyrrolo [3,2-e]pyrazolo[1,5-a]pyrimidine [$R_1$=(CH$_2$)$_3$CH$_3$, $R_2$=H, $R_3$=CN in formula (I)] (Compound 3 of this invention)
  Yield: 79.7%
  Melting Point: 143°–145° C
  Light yellowish orange crystals (iii) 8-iso-butyl-3-cyano-6,7-dihydro-5-methyl-8H-pyrrolo [3,2-e]pyrazolo[1,5-a]pyrimidine [$R_1$=CH$_2$CH(CH$_3$)$_2$, $R_2$=H, $R_3$=CN in formula (I)] (Compound 4 of this invention)
  Yield: 78.1%
  Melting Point: 182°–184° C
  White crystals (iv) 8-sec-butyl-3-cyano-6,7-dihydro-5-methyl-8H-pyrrolo [3,2-e]pyrazolo[1,5-a]pyrimidine, [$R_1$=CH(CH$_3$)CH$_2$CH$_3$, $R_2$=H, $R_3$=CN in formula (I)] (Compound 5 of this invention)
  Yield: 74.1%
  Melting Point: 241°–243° C
  Slight yellowish green crystals (v) 3-cyano-6,7-dihydro-5-methyl-8-pentyl-8H-pyrrolo [3,2-e]pyrazolo[1,5-a]pyrimidine [$R_1$=(CH$_2$)$_4$CH$_3$, $R_2$=H, $R_3$=CN in formula (I)] (Compound 6 of this invention)
  Yield: 80.5%
  Melting Point: 139°–142° C
  Yellow crystals (vi) 3-cyano-6,7-dihydro-8-hexyl-5-methyl-8H-pyrrolo [3,2-e]pyrazolo[1,5-a]pyrimidine [$R_1$=(CH$_2$)$_5$CH$_3$, $R_2$=H, $R_3$=CN in formula (I)] (Compound 7 of this invention)
  Yield: 80.6%
  Melting Point: 125°–126° C
  Light yellowish orange rod like crystals (vii) 3-cyano-8-cyclopentyl-6,7-dihydro-5-methyl-8H-pyrrolo [3,2-e]pyrazolo[1,5-a]pyrimidine [$R_1$=CH(CH$_2$)$_4$, $R_2$=H, $R_3$=CN in formula (I)] (Compound 8 of this invention)
  Yield: 90.9%
  Melting Point: 240°–242° C
  Light yellowish orange crystals (viii) 3-cyano-8-cyclohexylmethyl-6,7-dihydro-5-methyl-8H-pyrrolo[3,2-e]pyrazolo[1,5-a]pyrimidine [$R_1$=CH$_2$CH(CH$_2$)$_5$, $R_2$=H, $R_3$=CN in formula (I)] (Compound 9 of this invention)
  Yield: 89.8%
  Melting Point: 217°–219° C
  Light yellow crystals

EXAMPLE 6

(i) A mixture of 0.40 g of Compound (VI) [$R_2$=C$_6$H$_5$, $R_3$=H], 0.40 g of anhydrous potassium carbonate, 0.14 g of tert-butylamine, and 3.5 ml of dimethylformamide was heated at 50°–60° C in a water bath for 5 hours while stirring. After cooling, 50 ml of chloroform was added and was filtered to eliminate insoluble substances. The filtrate was evaporated under reduced pressure. To the residue was added water and the mixture was extracted with chloroform. The chloroform layer was evaporated under reduced pressure and purified using thin layer chromatography. The crystals thus obtained were recrystallized in a mixed solvent of benzene and isopropanol to produce 0.13 g of 8-tert-butyl-6,7-dihydro-5-methyl-2-phenyl-8H-pyrrolo[3,2-e]pyrazolo[1,5-a]pyrimidine [$R_1$=C(CH$_3$)$_3$, $R_2$=C$_6$H$_5$, $R_3$=H in formula (I)] as light yellow crystals having a melting point of 244°–248° C at a yield of 27.0%.

The following compound was produced according to the same procedures as above.

(ii) 8-tert-butyl-6,7-dihydro-5-methyl-2-(3-thienyl)-8H-pyrrolo[3,2-e]pyrazolo[1,5-a]pyrimidine [$R_1$=C(CH$_3$)$_3$, $R_2$=

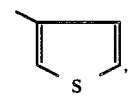

$R_3$=H in formula (I)]
  Yield: 24.0%
  Melting Point: 204°–207° C
  Light yellow crystals

EXAMPLE 7

A mixture of 16.11 g of Compound (VI) [$R_2$=H, $R_3$=H], 38 g of anhydrous potassium carbonate, 5.85 g of tert-butylamine, and 140 ml of dimethylformamide was heated at 50°–60° C in a water bath for 2 days while stirring. The reaction mixture was cooled and filtered. The filtrate was evaporated under reduced pressure. The residue was dissolved in 150 ml of chloroform. The chloroform layer was washed with water and evaporated under reduced pressure to obtain 15.72 g of an oily substance. The oily substance was purified using silica gel chromatography, followed by recrystallizing in a mixed solvent of benzene-isopropylether-hexane to produce 8-tert-butyl-6,7-dihydro-5-methyl-8H-pyrrolo[3,2-e]pyrazolo[1,5-a]pyrimidine [$R_1$=C(CH$_3$)$_3$, $R_2$=H, $R_3$=H in formula (I)] (Compound 11 of this invention) as light yellow plate crystals having a melting point of 147°–149° C at a yield of 70.1%.

EXAMPLE 8

(8-1) 2.20 g of 4-aminomorpholine was added to a mixture of 5.00 g of Compound (VI) [$R_2$=H, $R_3$=CN], 6 ml of triethylamine, 40 ml of dimethylformamide. The mixed solution was stirred at room temperature overnight. Crystals produced were filtered, washed with ethanol and recrystallized in a mixed solvent of chloroform and 2-propanol to obtain 3-cyano-6,7-dihydro-5-methyl-8-(4-morpholyl)-8H-pyrrolo[3,2-e]yrazolo[1,5-a]pyrimidine [$R_1$=

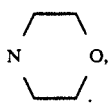

$R_2$=H, $R_3$=CN in formula (I)] (Compound 10 of this invention) as white plate crystals having a melting point of above 300° C at a yield of 86.5%.

The following compound was produced according to the same procedures as above.

(ii) 3-cyano-6,7-dihydro-8-(3,4-dimethoxyphenylethyl)-5-methyl-8H-pyrrolo[3,2-e]pyrazolo[1,5-a]pyrimidine

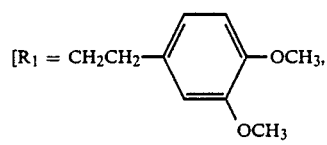

$R_2$ = H, $R_3$ = CN in fomrula (I)]

Yield: 80.2%
Melting Point: 172° C
White plate crystals

EXAMPLE 9

1.3 mmol of primary amine ($H_2N$-$R_1$) was added to a mixture of 2.55 g of Compound (VI) [$R_2$=H, $R_3$=CN], 5 ml of triethylamine, and 30 ml of ethanol. The mixture was refluxed under heating at 90°-100° C. in a water bath for 3 hours while stirring. After the reaction mixture was cooled, it was treated according to either process (a), (b), (c), (d), (e), or (f) to obtain the target Compounds (I) (Compounds 12-34) shown in Table 1 [$R_1$: listed in Table 1, $R_2$=H, $R_3$=CN]

(a) The crystals deposited were collected by filtration and recrystallized in a mixed solvent of isopropanol, water, and the solvents listed in the table.

(b) The above reaction mixture was evaporated under reduced pressure. Crude crystals obtained were recrystallized.

(c) The above reaction mixture was evaporated under reduced pressure. Crude crystals obtained were dissolved in 30 ml of chloroform. The solution was charged into a chromatographic column packed with 7.0 g of alumina (pH 9-11) and developed. The eluate was evaporated under reduced pressure, crystallized using ethyl acetate under cooling and further recrystallized.

(d) The above reaction mixture was condensed under reduced pressure. The residue was extracted with 30 ml of chloroform. The chloroform layer was washed with water, dried over anhydrous sodium sulfate, and charged into a chromatographic column packed with 10 g of alumina (pH 9-11). The eluate was condensed under reduced pressure and recrystallized.

(e) The above reaction mixture was condensed under reduced pressure. The residue was extracted with 80 ml of ethyl acetate. The extract was purified using a chromatographic column packed with 10 g of alumina (pH 9-11). The eluate was condensed under reduced pressure, crystallized in isopropylether, and recrystallized.

(f) The above reaction mixture was condensed under reduced pressure. The residue was extracted with 70 ml of ethyl acetate. The extract was washed with saturated brine. After drying using sodium sulfate, the product was condensed under reduced pressure and crystallized in isopropylether. The crystals thus obtained was recrystallized.

TABLE 1

| Compound No. | $R_1$ | M.P. (°C) | | Solvent | Yield (%) | Process |
|---|---|---|---|---|---|---|
| Compound 12 | —(CH₂)₂—pyrrolidine-N-CH₃ | 162 | Yellow plate crystals | EtOAc-IPE | 96.7 | (e) |
| Compound 13 | —N(piperazine)N—CH₃ | 297 | White crystals | Water | 67.3 | (a) |
| Compound 14 | —(CH₂)₂—N(CH₃)₂ | 177-178 | Yellowish green plate crystals | EtOAc-IPE | 85.1 | (b) |
| Compound 15 | —(CH₂)₂—N(C₂H₅)₂ | 114 | Yellowish green plate crystals | EtOAc-IPE | 83.9 | (e) |

EtOAc: ethylacetate   CHCl₃: chloroform
IPE: isopropylether   DMF: dimethylformamide
IPA: isopropyl alcohol
MeOH: methanol ($R_2$ = H)
($R_3$ = CN)

TABLE 1-continued

[Structure shown with R1, R2=H, R3=CN, CH3 substituents on fused ring system]

(R2 = H)
(R3 = CN)

EtOAc: ethylacetate    CHCl3: chloroform
IPE: isopropylether    DMF: dimethylformamide
IPA: isopropyl alcohol
MeOH: methanol

| Compound No. | R1 | M.P. (°C) | | Solvent | Yield (%) | Process |
|---|---|---|---|---|---|---|
| Compound 16 | −(CH2)2−N(CH(CH3)2)2 | 138 | Yellowish green plate crystals | EtOAc-IPE | 92.0 | (e) |
| Compound 17 | −(CH2)2−N(pyrrolidine) | 176–177 | White needle crystals | EtOAc-IPE | 84.5 | (b) |
| Compound 18 | −(CH2)2−N(4-methylpiperidine) | 132 | Yellow plate crystals | EtOAc-IPE | 29.6 | (e) |
| Compound 19 | −CH2−(N-ethylpyrrolidin-2-yl) | 159–160 | White crystals | MeOH-EtOAc | 80.9 | (e) |
| Compound 20 | −(CH2)3−N(CH3)2 | 116 | Yellowish green plate crystals | IPA-EtOAc | 88.0 | (a) |
| Compound 21 | −(CH2)3−N(C2H5)2 | 109 | Yellowish green plate crystals | IPA-EtOAc | 86.5 | (e) |
| Compound 22 | −(CH2)3−N((CH2)3CH3)2 | 85–86 | Yellowish green plate crystals | IPE-n-Hexane | 81.5 | (e) |
| Compound 23 | −(CH2)3−N(piperidine) | 156 | White needle crystals | EtOAc-IPE | 77.2 | (e) |
| Compound 24 | −(CH2)3−N(2-methylpiperidine) | 141 | Yellowish green plate crystals | IPA-AcOEt | 91.7 | (a) |
| Compound 25 | −(CH2)3−N(4-methylpiperidine) | 142 | Yellowish green plate crystals | IPA-AcOEt | 92.0 | (e) |
| Compound 26 | −CH(CH3)−(CH2)3−N(C2H5)2 | 129 | Yellowish plate crystals | IPA-IPE | 79.4 | (a) |

TABLE 1-continued

[Structure diagram with N—R₁, CH₃, N, R₂, R₃ substituents on a pyrrolopyrazolopyrimidine skeleton]

(R₂ = H)
(R₃ = CN)

EtOAc: ethylacetate  CHCl₃: chloroform
IPE: isopropylether  DMF: dimethylformamide
IPA: isopropyl alcohol
MeOH: methanol

| Compound No. | R₁ | M.P. (°C) | | Solvent | Yield (%) | Process |
|---|---|---|---|---|---|---|
| Compound 27 | —(CH₂)₂—N(morpholino) | 149–150 | Yellowish green plate crystals | IPA | 89.7 | (d) |
| Compound 28 | —(CH₂)₃—N(morpholino) | 142 | Yellowish green plate crystals | IPA-EtOAc | 92.0 | (e) |
| Compound 29 | —(CH₂)₂—(N-methylpyrrolyl) | 158 | Yellowish green plate crsytals | EtOAc | 88.2 | (b) |
| Compound 30 | —(CH₂)₂—(2-pyridyl) | 160–161 | Yellowish green plate crystals | CHCl₃-EtOAc | 90.0 | (c) |
| Compound 31 | —(CH₂)₃—(imidazolyl) | 242 | White crystals | DMF-EtOH | 90.0 | (a) |
| Compound 32 | —(CH₂)₃—O—(CH₂)₂—N(CH₃)₂ | 81 | White crystals | EtOAc-IPE | 92.9 | (f) |
| Compound 33 | —(CH₂)₃—N(2-pyrrolidinonyl) | 175 | White crystals | EtOH-Water | 92.6 | (f) |
| Compound 34 | —CH₂—CH(OH)—CH₂—OH | 185 | White plate crystals | MeOH-EtOH | 91.6 | (d) |

Hereinafter are presented experimental examples to further illustrate the effectiveness of the invention. These examples are given for illustration of the invention and are not intended to be limiting thereof.

EXPERIMENTAL EXAMPLES

Experimental Example 1

Vasodilative activity of the compound of the present invention was measured by the Magnus method. Trapidil [Japanese Journal of Pharmacology, 76, 495–503 (1980)] was used as a control.

A bastard, male, adult dog weighing about 8–10 kg was anesthetized with pentobarbital sodium (25 mg/kg, i.v.) and killed by bleeding. Its basilar and coronary arteries were immediately extracted. A ring, 4–5 mm wide, was made from the vessels, and 2 g of a load was applied to the vessel ring in an organic bath filled with 10 ml of a Krebs-Henseleit solution (NaCl 118 mM, KCl 4.75 mM, $CaCl_2$ 2.54 mM, $KH_2PO_4$ 1.19 mM, $MgSO_4$ 1.19 mM, $NaHCO_3$ 12.5 mM, and glucose 10.0 mM) which had been aerated with a mixed gas ($O_2$ 95%, $CO_2$ 5%) at 37° C. Static tensions of the ring were isometrically measured and recorded.

Test compounds were accumulatively given to specimens contracted with $1 \times 10^{-7}$M (final concentration) U-46619 to the final concentration of $1 \times 10^{-7}$ to $1 \times 10^{-4}$M to investigate their vasodilative activities.

Table 2 shows 50% contraction-inhibitive concentrations for the basilar artery of 8-tert-butyl-3-cyano-6,7-dihydro-5-methyl-8H-pyrrolo[3,2-e]pyrazolo[1,5-a]pyrimidine (Compound No. 1), 8-tert-butyl-3-cyano-6,7-dihydro-2,5-dimethyl-8H-pyrrolo[3,2- e]pyrazolo[1,5-a]pyrimidine (Compound No. 2), and trapidil. Both Compound Nos. 1 and 2 exhibited a vasodilative activity 37 times stronger than trapidil.

Table 3 shows 50% contraction-inhibitive concentrations for the coronary artery of Compound Nos. 1 and 2, and trapidil. Compound Nos. 1 and 2 respectively exhibited a 39 times and a 35 times stronger vasodilative activity than trapidil.

TABLE 2

| Tested Compounds | 50% Contraction-inhibitive Concentrations |
| --- | --- |
| Compound No. 1 | $2.7 \times 10^{-6}$ M |
| Compound No. 2 | $2.7 \times 10^{-6}$ M |
| Trapidil | $1.0 \times 10^{-4}$ M |

TABLE 3

| Tested Compounds | 50% Contraction-inhibitive Concentrations |
| --- | --- |
| Compound No. 1 | $1.6 \times 10^{-6}$ M |
| Compound No. 2 | $1.8 \times 10^{-6}$ M |
| Trapidil | $6.3 \times 10^{-5}$ M |

Experimental Example 2

The vasodilative activity and coronary blood flow increase activity were respectively measured according to the following Methods 1 and 2. Trapidil was used as a control.

<Method 1>

The same Magnus method was used as in Experimental Example 1, except that instead of $1 \times 10^{-7}$M (final concentration) U-46619, $5 \times 10^{-6}$M (final concentration), PGF$_2\alpha$ or 60 mM potassium chloride was used. The results are shown in Table 4.

right femoral artery pressure, and lower extremity blood flow rate were monitored. All test compounds were intravenously administered.

The maximum coronary blood flow rates achieved after the administration as a percentage of the blood flow before administration was taken as the coronary blood flow increase activity. The results are shown in Table 5.

TABLE 5

| | Rate of Coronary Blood Flow Increase (%) | |
| --- | --- | --- |
| Tested Compounds | 50 μg/kg (iv) | 100 μg/kg (iv) |
| Compound No. 1 | 51.9 ± 11.9 | 181.6 ± 27.8 |
| Compound No. 3 | 11.5 ± 4.6 | 37.9 ± 16.3 |
| Compound No. 4 | 20.4 ± 6.3 | 52.8 ± 21.1 |
| Compound No. 5 | 8.2 ± 3.7 | 27.3 ± 5.2 |
| Compound No. 6 | 7.3 ± 3.1 | 15.4 ± 5.7 |
| Trapidil | 8.7 ± 2.5 | 14.0 ± 2.21 |

Experimental Example 3

Tracheal expansion activity against tracheal contraction induced by acetyl choline (ACh) and histamine (His)

A Hartley guinea pigs (male, weight: 400–500 g) was killed by bleeding and its trachea was immediately extracted. Extracted trachea specimens prepared according to the method of Takagi et al. [Chem. Pharm. Bull., 6, 716–720 (1958)] were suspended with a 0.5 g load in an organic bath filled with a Krebs-Henseleit solution (NaCl 118 mM, KCl 4.75 mM, CaCl$_2$ 2.54 mM, KH$_2$PO$_4$ 1.19 mM, MgSO$_4$ 1.19 mM, NaHCO$_3$ 12.5 mM, and glucose 10.0 mM) which had been aerated with a mixed gas (O$_2$ 95%, CO$_2$ 5%). Static tensions was isometrically measured.

Test compounds were applied to specimens con-

TABLE 4

| | 50% Contraction-inhibitive Concentrations | | | |
| --- | --- | --- | --- | --- |
| | Basilar Artery | | Coronary Artery | |
| Tested Compounds | PGF$_2\alpha$ | KCl | PGF$_2\alpha$ | KCl |
| Compound No. 1 | $1.6 \times 10^{-6}$ M | $>1 \times 10^{-4}$ M | $1.3 \times 10^{-6}$ M | $>1 \times 10^{-4}$ M |
| Compound No. 3 | $>1 \times 10^{-4}$ M | $3.4 \times 10^{-5}$ M | $>1 \times 10^{-4}$ M | $>1 \times 10^{-4}$ M |
| Compound No. 4 | $>1 \times 10^{-4}$ M | $4.3 \times 10^{-5}$ M | $2.5 \times 10^{-5}$ M | $1 \times 10^{-4}$ M |
| Compound No. 5 | $2.5 \times 10^{-6}$ M | $>1 \times 10^{-4}$ M | $3.2 \times 10^{-6}$ M | $>1 \times 10^{-4}$ M |
| Compound No. 6 | $>1 \times 10^{-4}$ M | $>1 \times 10^{-4}$ M | $>1 \times 10^{-4}$ M | $>1 \times 10^{-4}$ M |
| Compound No. 7 | $>1 \times 10^{-4}$ M | $8.5 \times 10^{-5}$ M | $>1 \times 10^{-4}$ M | $>1 \times 10^{-4}$ M |
| Compound No. 8 | $>1 \times 10^{-4}$ M | $>1 \times 10^{-4}$ M | $2 \times 10^{-7}$ M | $>1 \times 10^{-4}$ M |
| Compound No. 9 | $>1 \times 10^{-4}$ M | $>1 \times 10^{-4}$ M | $>1 \times 10^{-4}$ M | $>1 \times 10^{-4}$ M |
| Compound No. 10 | $>1 \times 10^{-4}$ M | $>1 \times 10^{-4}$ M | $>1 \times 10^{-4}$ M | $>1 \times 10^{-4}$ M |
| Compound No. 11 | $7.9 \times 10^{-6}$ M | $1.0 \times 10^{-5}$ M | $3.2 \times 10^{-6}$ M | $1.6 \times 10^{-5}$ M |
| Trapidil | $>1 \times 10^{-4}$ M | $>1 \times 10^{-4}$ M | $>1 \times 10^{-4}$ M | $>1 \times 10^{-4}$ M |

*Compound 3: 8-butyl-3-cyano-6,7-dihydro-5-methyl-8H-pyrrolo[3,2-e]pyrazolo[1,5-a]pyrimidine
Compound 4: 8-iso-butyl-3-cyano-6,7-dihydro-5-methyl-8H-pyrrolo[3,2-e]pyrazolo[1,5-a]pyrimidine
Compound 5: 8-sec-butyl-3-cyano-6,7-dihydro-5-methyl-8H-pyrrolo[3,2-e]pyrazolo[1,5-a]pyrimidine
Compound 6: 3-cyano-6,7-dihydro-5-methyl-8-pentyl-8H-pyrrolo[3,2-e]pyrazolo[1,5-a]pyrimidine
Compound 7: 3-cyano-6,7-dihydro-8-hexyl-5-methyl-8H-pyrrolo[3,2-e]pyrazolo[1,5-a]pyrimidine
Compound 8: 3-cyano-8-cyclopentyl-6,7-dihydro-5-methyl-8H-pyrrolo[3,2-e]pyrazolo[1,5-a]pyrimidine
Compound 9: 3-cyano-8-cyclohexylmethyl-6,7-dihydro-5-methyl-8H-pyrrolo[3,2-e]pyrazolo[1,5-a]pyrimidine
Compound 10: 3-cyano-6,7-dihydro-5-methyl-8-(4-morpholyl)-8H-pyrrolo[3,2-e]pyrazolo[1,5-a]pyrimidine
Compound 11: 8-tert-butyl-6,7-dihydro-5-methyl-8H-pyrrolo[3,2-3]pyrazolo[1,5-a]pyrimidine <Method 2>

A bastard, male, adult dog weighing about 10–15 kg was anesthetized with pentobarbital sodium (25 mg/kg, i.v.) and respirated with a tracheal cannula. The heart was exposed by an incision into pericardium through the left quartus costa rib. About 1 cm of a coronary vessel was peeled off from the surrounding tissues at about 1 cm from the left ramus circumplexus and a blood flow meter probe was installed for measuring the coronary blood flow. Left ventricle pressure, heart rate, tracted with $1 \times 10^{-6}$M (final concentration) ACh or His to the final concentration of $1 \times 10^{-7}$–$1 \times 10^{-4}$ to investigate their tracheal expansion activities.

Table 6 shows 50% contraction-inhibitive concentrations of pyrrolo[3,2-e]pyrazolo[1,5-a]pyrimidine derivatives and theophylline against ACh- or His-induced contraction, and a reverse ratio of the 50% contraction-inhibitive concentration of each derivative for that of theophylline (Ratio of Effectiveness).

TABLE 6

| Compounds | 50% Contraction-inhibitive Concentration (M) | | Ratio of Effectiveness | |
|---|---|---|---|---|
| | ACh Contraction | His Contraction | ACh Contraction | His Contraction |
| Compound No. 1 | $2.0 \times 10^{-7}$ | $1.3 \times 10^{-6}$ | 25.0 | 4.9 |
| Compound No. 3 | — | $3.0 \times 10^{-5}$ | — | 2.1 |
| Compound No. 5 | $5.0 \times 10^{-7}$ | $4.0 \times 10^{-7}$ | 10.0 | 15.8 |
| Compound No. 6 | $3.2 \times 10^{-6}$ | $1.6 \times 10^{-5}$ | 1.6 | 0.4 |
| Compound No. 7 | $6.3 \times 10^{-6}$ | $1.3 \times 10^{-5}$ | 0.8 | 0.5 |
| Compound No. 8 | $1.3 \times 10^{-7}$ | $1.0 \times 10^{-6}$ | 38.5 | 6.3 |
| Compound No. 9 | $7.9 \times 10^{-7}$ | — | 6.3 | — |
| Compound No. 10 | $1.3 \times 10^{-6}$ | $5.0 \times 10^{-6}$ | 3.9 | 1.3 |
| Compound No. 11 | — | $6.3 \times 10^{-6}$ | — | 1.0 |
| Theophylline | $5.0 \times 10^{-6}$ | $6.3 \times 10^{-6}$ | 1.0 | 1.0 |

Experimental Example 4

An acute toxicity test on compounds of the present invention was performed according to the following method.

ICR male mice were purchased at 4 weeks of age and fed for 10 days before testing. The test compound suspended in 1% methylcellullose solution was orally administered using a metallic gaster probe at a dose of 0.1 ml (as the test compound) per 10 kg of body weight. The mice were fasted for 15 hours before the administration. Observation was made for 14 days after the administration, and the $LD_{50}$ value was determined from the survival rate by the Richfield Wilcoxin method. As a result $LD_{50}$ for Compound Nos. 1 and 2 was found to be 2 g/kg or more and for Compound Nos. 3–11 1 g/kg or more.

Hereinafter are presented formulation examples. These examples are given for illustration of the invention and are not intended to be limiting thereof.

FORMULATION EXAMPLES

| Formulation Example 1 | |
|---|---|
| Compound No. 8 | 25 g |
| Lactose | 130 g |
| Crystalline cellulose | 20 g |
| Corn starch | 20 g |
| 3% aqueous hydroxypropyl cellulose | 100 ml |
| Magnesium stearate | 2 g |

Compound No. 8, lactose, crystalline cellulose, and corn starch were screened through a 60-mesh sieve, homogenized, and charged into a kneader. The 3% aqueous solution of hydroxypropyl cellulose was added and the mixture was kneaded. The product was granulated by a 16-mesh sieve, dried in air at 50° C, and again granulated by a 16-mesh sieve. Magnesium stearate was added to the granule and mixed. The mixture was tableted to produce tablets weighing 200 mg each and having an 8 mm diameter.

| Formulation Example 2 | |
|---|---|
| Compound No. 1 | 25 g |
| Lactose | 130 g |
| Crystalline cellulose | 20 g |
| Corn starch | 20 g |
| 3% aqueous hydroxypropyl cellulose | 100 ml |
| Magnesium stearate | 2 g |

Compound No. 1, lactose, crystalline cellulose, and corn starch were screened through a 60-mesh sieve, homogenized, and charged into a kneader. The 3% aqueous solution of hydroxypropyl cellulose was added and the mixture was kneaded. The product was granulated by a 16-mesh sieve, dried in air at 50° C, and again granulated by a 16-mesh sieve. Magnesium stearate was added to the granule and mixed. The mixture was tableted to produce tablets weighing 200 mg each and having an 8 mm diameter.

| Formulation Example 3 | |
|---|---|
| Compound No. 5 | 25 g |
| Lactose | 125 g |
| Corn starch | 48.5 g |
| Magnesium stearate | 1.5 g |

The above components were finely pulverized and thoroughly mixed to produce a homogeneous mixture. The mixture was filled in gelatin capsules, 0.2 g per capsule, to obtain capsules for oral administration.

Obviously, numerous modifications and variations of the present invention are possible in light of the above teachings. It is therefore to be understood that within the scope of the appended claims, the invention may be practiced otherwise than as specifically described herein.

What is claimed is:

1. A pyrrolo(3,2-e)pyrazolo(1,5-a)pyrimidine having formula (I):

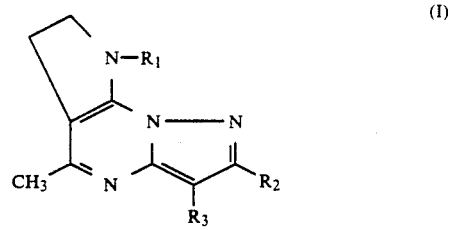

(I)

wherein $R_1$ and $R_2$, individually, are hydrogen, linear or branched $C_{1-14}$ alkyl, $C_{4-8}$ cycloalkyl, phenyl, pyrrole, pyrrolidine, pyridine, piperidine, imidazole, imidazoline, morpholine or pyrrolidone; a $C_{1-14}$ alkyl, $C_{4-8}$ cycloalkyl, phenyl, pyrrole, pyrrolidine, pyridine, piperidine, imidazole, imidazoline, morpholine or pyrrolidone substituted with a hydroxyl, alkoxy, nitro, primary amino, secondary amino, tertiary amino, carboxyl, $C_{4-8}$ cycloalkyl, phenyl, halogen, pyrrole, pyrrolidine, pyridine, piperidine, imidazole, imidazoline, morpholine or pyrrolidone group, and $R_3$ is a hydrogen or cyano; or a salt thereof.

2. The pyrimidine of claim 1, wherein $R_1$ or $R_2$ are said linear or branched $C_{1-14}$ alkyl or substituted linear or branched $C_{1-14}$ alkyl.

3. The pyrimidine of claim 1, wherein $R_1$ or $R_2$ are said $C_{4-8}$ cycloalkyl or said substituted $C_{4-8}$ cycloalkyl.

4. The pyrimidine of claim 1, wherein $R_1$ or $R_2$ is said heterocyclic or said substituted heterocyclic group.

5. The pyrimidine of claim 1, wherein $R_3$ is hydrogen.

6. The pyrimidine of claim 1, wherein $R_3$ is cyano.

7. A pharmaceutical composition comprising an effective amount of a pyrrolo[3,2-e]pyrazolo[1,5-a]pyrimidine having formula (I),

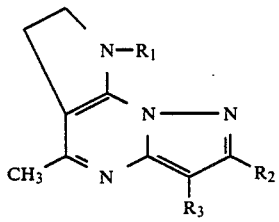

(I)

wherein $R_1$ and $R_2$, individually, are hydrogen, linear or branched $C_{1-14}$ alkyl, $C_{4-8}$ cycloalkyl, phenyl, pyrrole, pyrrolidine, pyridine, piperidine, imidazole, imidazoline, morpholine or pyrrolidone; a $C_{1-14}$ alkyl, $C_{4-8}$ cycloalkyl, phenyl, pyrrole, pyrrolidine, pyridine, piperidine, imidazole, imidazoline, morpholine or pyrrolidone substituted with a hydroxyl, alkoxy, nitro, primary amino, secondary amino, tertiary amino, carboxyl, $C_{4-8}$ cycloalkyl, phenyl, halogen, pyrrole, pyrrolidine, pyridine, piperidine, imidazole, imidazoline, morpholine or pyrrolidone group, and $R_3$ is a hydrogen or cyano; or a pharmaceutically acceptable salt thereof and a pharmaceutical carrier.

8. The pharmaceutical compositions of claim 7, wherein $R_1$ or $R_2$ are said linear or branched $C_{1-14}$ alkyl or substituted linear or branched $C_{1-14}$ alkyl.

9. The pharmaceutical composition of claim 7, wherein $R_1$ or $R_2$ are said $C_{4-8}$ cycloalkyl or said substituted $C_{4-8}$ cycloalkyl.

10. The pharmaceutical composition of claim 7, wherein $R_1$ or $R_2$ is said heterocyclic or said substituted heterocyclic group.

11. The pharmaceutical composition of claim 7, wherein $R_3$ is hydrogen.

12. The pharmaceutical compositions of claim 7, wherein $R_3$ is cyano.

13. A method for treating circulatory disease, comprising administering to a patient in need thereof, an effective amount of a pyrrolo[3,2-e]pyrazolo[1,5-a]pyrimidine having formula (I),

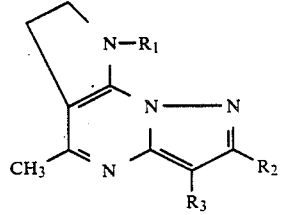

(I)

wherein $R_1$ and $R_2$, individually, are hydrogen, linear or branched $C_{1-14}$ alkyl, $C_{4-8}$ cycloalkyl, phenyl, pyrrole, pyrrolidine, pyridine, piperidine, imidazole, imidazoline, morpholine or pyrrolidone; a $C_{1-14}$ alkyl, $C_{4-8}$ cycloalkyl, phenyl, pyrrole, pyrrolidine, pyridine, piperidine, imidazole, imidazoline, morpholine or pyrrolidone substituted with a hydroxyl, alkoxy, nitro, primary amino, secondary amino, tertiary amino, carboxyl, $C_{4-8}$ cycloalkyl, phenyl, halogen, pyrrole, pyrrolidine, pyridine, piperidine, imidazole, imidazoline, morpholine or pyrrolidone group, and $R_3$ is a hydrogen or cyano; or a salt thereof.

14. A method for treating bronchiectasis, comprising administering to a patient in need thereof, an effective amount of a pyrrolo[3,2-e]pyrazolo[1,5-a]pyrimidine having formula (I),

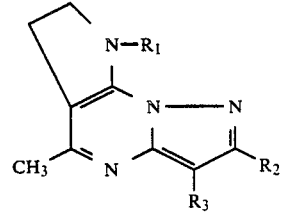

(I)

wherein $R_1$ and $R_2$, individually, are hydrogen, linear or branched $C_{1-14}$ alkyl, $C_{4-8}$ cycloalkyl, phenyl, pyrrole, pyrrolidine, pyridine, piperidine, imidazole, imidazoline, morpholine or pyrrolidone; a $C_{1-14}$ alkyl, $C_{4-8}$ cycloalkyl, phenyl, pyrrole, pyrrolidine, pyridine, piperidine, imidazole, imidazoline, morpholine or pyrrolidone substituted with a hydroxyl, alkoxy, nitro, primary amino, secondary amino, tertiary amino, carboxyl, $C_{4-8}$ cycloalkyl, phenyl, halogen, pyrrole, pyrrolidine, pyridine, piperidine, imidazole, imidazoline, morpholine or pyrrolidone group, and $R_3$ is a hydrogen or cyano; or a salt thereof.

* * * * *